United States Patent [19]

Kutter

[11] 4,180,060

[45] Dec. 25, 1979

[54] DEVICE FOR STAINING BIOLOGICAL MATERIALS

[75] Inventor: Dolphe Kutter, Rue Beck, Luxembourg

[73] Assignee: Boehringer Mannheim GmbH, Mannheim-Waldhof, Fed. Rep. of Germany

[21] Appl. No.: 822,964

[22] Filed: Aug. 8, 1977

Related U.S. Application Data

[63] Continuation of Ser. No. 385,000, Aug. 2, 1973, abandoned.

[30] Foreign Application Priority Data

Aug. 18, 1972 [DE] Fed. Rep. of Germany ....... 2240672

[51] Int. Cl.² ............................................... A61B 5/14
[52] U.S. Cl. .................................................... 128/760
[58] Field of Search ............... 128/2 G, 2 F, DIG. 5; 23/253 R, 253 TP, 259, 292; 73/425.4 P

[56] References Cited

U.S. PATENT DOCUMENTS

| | | | |
|---|---|---|---|
| 3,146,163 | 8/1964 | Brewer | 128/DIG. 5 |
| 3,322,114 | 5/1967 | Portnoy et al. | 128/DIG. 5 |
| 3,732,079 | 5/1973 | Davis | 23/253 TP |
| 3,768,978 | 10/1973 | Grubb et al. | 128/2 G |
| 3,952,599 | 4/1975 | Ayres | 73/425.4 P |

*Primary Examiner*—William E. Kamm
*Attorney, Agent, or Firm*—Sprung, Felfe, Horn, Lynch & Kramer

[57] ABSTRACT

Thin tubelets coated on their inner wall with a solid coating of a dyestuff or staining reagent are used to stain biological material by passing such material through the tubelet, optionally after mixing with a solvent, and allowing the biological material to react in the tubelet with the dyestuff or staining reagent.

5 Claims, No Drawings

DEVICE FOR STAINING BIOLOGICAL MATERIALS

This is a continuation of application Ser. No. 385,000, filed Aug. 2, 1973, now abandoned.

The present invention is concerned with a device for the staining of biological material for microscopic investigation.

The microscopic assessment of biological materials, such as blood, urine, bacterial cultures, body secretions and the like is part of the daily routine of medical and clinical laboratories. This assessment is simplified and, in many cases, first made possible by a particular staining of individual components. Many such staining methods have been known for quite a long time. Most of them are relatively complicated since they involve several steps, such as fixing, staining and washing the materials on a microscope slide. Consequently, they usually need to be carried out in well-equipped laboratories by trained personnel.

Attempts have certainly been made to simplify the complicated staining processes in order that they can also be carried out in smaller laboratories and in medical practices by untrained personnel. A known example is the so-called vital staining of reticulocytes with pre-colored microscope slides (cf. Pschyrembel, Klinisches Wörterbuch, Berlin, 1969, p. 1287).

In this case, a microscope slide is coated with a solution of 1 g. brilliant cresyl blue in 100 ml. alcohol and dried. A drop of blood is placed on the coated microscope slide or blood is spread out on the slide by placing a cover slip on it. After about 10 minutes, the staining process is finished and the preparation can be examined under a microscope.

Even though this process appears to be simple, in practice it suffers from the following serious disadvantages:

Thin layers dry extremely quickly so that the microscope slide must be kept in a humid chamber during the staining process. However, such a humid chamber is not generally available so that provision thereof entails a troublesome additional expenditure. If the staining is carried out under a cover slip, then it is not possible to store the preparation since, even after covering with a cover slip, a blood preparation will dry out and thus become useless. A subsequent assessment, which can be advantageous or desirable, or even a dispatch of the preparation, which is often necessary or desirable, is, therefore, not possible.

Blood intended for staining is usually taken from the finger tip or ear lobe of the patient and applied to the pre-colored microscope slide. If the staining proves to be unsuccessful or for some other reason is useless or requires to be repeated, then a fresh sample of blood must be taken from the patient. This usually means that the patient must be brought back again because very often he will have gone away.

The present invention provides a simple and universally applicable staining process for biological material, which can readily be carried out by untrained personnel, which ensures a satisfactory, uniform staining for microscopic investigation, which does not require the use of additional apparatus, such as developing chambers, and which permits storage of the sample for subsequent investigation or for dispatch.

It has, surprisingly, been found that all these advantages can be realized in a simple manner by the instant invention.

Essentially, the invention comprises carrying out the staining in a thin tubelet or in a capillary, the inner wall of which is coated with the dyestuffs or reagents necessary for the staining.

Thus, the present invention provides a method for staining biological materials, comprising introducing the biolgial material to be investigated, optionally after mixing with a solvent, into a tubelet, the inner wall of which is coated with a solid coating of appropriate dyestuffs or reagents, allowing the material to react in the tubelet with the dyestuffs or reagents and, after transferring same to a microscope slide, examining the resulting stained material in the usual manner.

The present invention also provides a device for staining biological materials, consisting of a thin tubelet or capillary, the inner wall of which is coated with a solid coating of appropriate dyestuffs or reagents.

The use of internal-coated tubelets can, in principle, be applied to all known staining processes, if certain prerequisites are fulfilled:

1. The material to be investigated must be sufficiently fluid to pass into the tubelet; insufficiently fluid material can, if necessary, be slurried with an appropriate liquid, for example, faeces with water.
2. The dyestuff or staining reagents must be at least somewhat soluble in the fluid to be investigated, for example in blood or urine, in order that staining can proceed quickly; solubilizing materials, such as polyglycols or the like, can optionally be added; when staining blood, an anti-coagulant, such as heparin, ethylenediamine-tetraacetic acid or sodium citrate, is added to the dyestuff or staining reagent.

Thus, for example, the following known dyeing processes can be carried out with the device according to the present invention:

methylene blue staining of reticulocytes, leucocytes and thrombocytes;
nile blue sulfate staining of Heinz bodies;
Sternheimer-Malbin staining (gentian violet and safranin) of urine sediment;
Seyderhelm's staining (trypan blue and Congo red) for leucocyte differentiation in urine sediment;
haematocrit by Seeman's method with neutral red and Janus green B;
staining of starch in gastric juice with Lugol's solution ($KI-I_2$);
peroxidase staining of Gonococci with p-phenylenediamine;
fuchsin staining of bacteria in urine;
nitro blue tetrazolium (NBT) test for phagocytic leucocytes.

The device according to the present invention can be produced in a simple manner by dissolving the dyestuffs or staining reagents needed for the staining, possibly together with anti-coagulants, buffers, solubilizing agents, preservation agents and the like, in readily volatile solvents, usually in water, lower alcohols or the like. If necessary, the solvent used can also contain a viscosity-regulating material. The solution is drawn or forced through thin tubelets and thereafter is dried or warm air or an inert gas is drawn or blown therethrough until all of the solvent has evaporated and a solid residue of the staining reagent remains behind, adhering to the inner wall of the tubelet.

A uniform coating of the inner wall of the tubelet is not absolutely necessary but in a large-scale production of the tubelets, uniform application enables a better reproducibility to be achieved during production.

The coating of the tubelets can be carried out in a large variety of ways, methods which can be used on a large scale being preferred. Thus, for example, long capillaries, such as are obtained by drawing, can first be coated and then cut up into pieces of appropriate length or short pieces of capillary can first be produced and these then coated with appropriate devices.

The concentration of the dyestuffs or of the staining reagents in the coating solution depends, of course, upon the internal diameter of the capillaries to be coated and upon the amount of biological fluid which is to be stained. It can either be calculated or determined by simple experiments, having regard to the concentrations of the known dyestuff solutions. The individual components of the staining reagents can be introduced into the capillary either together or successively, especially when they are not all soluble in the same solvent.

The tubelets used are preferably made of glass but other materials, for example synthetic resins, can also be used if they do not affect the staining reagents. Thus, for example, the staining reagents must not draw irreversibly on to the synthetic resins.

Normally, simple, transparent tubelets are used. In special cases, opaque or colored tubelets can be employed in order, for example, to provide a protection against the action of light.

In comparison with the process of staining on predyed microscope slides, the process according to the present invention has the following advantages:

1. The dyestuffs or staining reagents are present in the interior of a vessel with very small openings. Thus, they are protected against contact, the effect of dust and the like. In the case of sensitive reagents, the capillaries can even be sealed or otherwise closed and, if necessary, can be filled with a gas. The closed ends are then simply broken off before use.
2. The thickness of the layers on the inner walls of the capillaries is, as we have found from experience, very uniform, which is attributable to adhesion on the small rounded internal surface and this permits a good reproducibility. Uniform and thus reproducible coatings of solutions of low viscosity on plane surfaces, such as microscope slides, are, as is known from experience, much more difficult to achieve.
3. When, after drawing in the liquid to be investigated, the tubelets are temporarily closed, for example with wax, or more or less permanently closed, for example with a sealing lacquer or by fusing, then the capillaries can easily be transported, for example from the sampling point to the laboratory. During this time, the staining process can even have taken place so that it is possible immediately to commence microscopic examination in the laboratory. If desired or if necessary, such filled and closed tubelets can also be sent by post.
4. The tubelets filled with the fluid to be investigated can also be closed at one end and centrifuged in an appropriate centrifuge, for example in a haematocrit centrifuge. In this way, further special effects can be achieved, such as a further concentrating of a sparse urine sediment.

Although the main field of use of the process and device according to the present invention is in human medicine, it can, of course, also be used in other fields. Thus, for example, it is of considerable value in veterinary medicine, in the examination of foodstuffs, in zoology, in bacteriology and the like.

The following Examples are given for the purpose of illustrating the present invention:

EXAMPLE 1

Vital Dyeing of Reticulocytes

Through a capillary of 75 mm. length and about 1 mm. diameter (for example a commercially-available haematocrit tubelet), the inner wall of which was coated with heparin, there was drawn a 2% solution of brilliant cresyl blue in methanol and thereafter dry air was drawn through for about 2 minutes. In this state, the tubelets could be stored for an almost unlimited time.

Blood was drawn into this tubelet (about 30 mm. length of blood) from the finger tip or ear lobe of a patient. Thereafter, the tubelet was tilted backwards and forwards a few times and then left for 10 minutes. Thereafter, a part of the stained blood was applied to a microscope slide and examined microscopically in the usual manner. The reticulocytes could be recognized as dark blue granule-containing erythrocytes.

The same results were obtained when, instead of brilliant cresyl blue, there was used a 1% methanolic solution of new methylene blue.

EXAMPLE 2

Nile Blue Dyeing of Heinz Bodies

When, as described in Example 1, a capillary was treated with a 1% methanolic solution of Nile blue sulfate, then a capillary was obtained in which, besides the reticulocytes, the Heinz intracorpuscular bodies of the erythrocytes could be stained blue.

EXAMPLE 3

Urine Sediment Dyeing by Sternheimer and Malbin's Method

Through a glass capillary of about 70 mm. length and about 1 mm. diameter (for example a melting point tube), there was drawn the following solution and thereafter air was sucked through until the capillary was dry:

crystal violet—0.1 ml.
safranin T—0.3 ml.
methanol—ad 100.0 ml.

When some urine centrifugate was drawn into this capillary, the capillary shaken backwards and forwards a few times and the contents thereof then applied to a microscope slide, under a microscope there could be observed the known picture of the Sternheimer-Malbin sediment staining.

After drawing in the urine sediment, the capillary could also be closed at one end with wax and centrifuged in an appropriate centrifuge. When the wax was removed and the centrifugate carefully placed on a microscope slide, then the solid bodies of the urine were obtained in a particularly large number.

EXAMPLE 4

Peroxidase Dyeing of Gonococci

Through a glass capillary of about 70 mm. length and about 1 mm. diameter, there was forced a 5% ethanolic solution of freshly distilled p-phenylenediamine and the capillary subsequently blown dry with a current of nitrogen. Thereafter, both ends of the capillary were sealed with a sealing lacquer, whereafter the capillary was of almost unlimited storage stability. Before use, both ends of the capillary were broken off and some pus, diluted with water, allowed to draw in. The capillary was moved backwards and forwards a few times and kept at 37° C. for about an hour. Thereafter, the contents of the capillary were examined microscopically: The Gonococci were stained black.

It will be understood that the specification and examples are illustrative but not limitative of the present invention and that other embodiments within the spirit and scope of the invention will suggest themselves to those skilled in the art.

What is claimed is:

1. Device for staining individual cells suspended in a biological fluid, consisting essentially of a thin tubelet and a solid coating of staining reagent for uniformly staining the suspended individual cells, which coating is applied to the inner wall of said tubelet and which is soluble in said fluid, whereby the uniform staining of the suspended individual cells for microscopic examination is effected upon removal of the reagent from the inner wall of said tubelet when dissolved in said fluid.

2. Device as claimed in claim 1, wherein the inner diameter of said tubelet is about 0.3 mm. to 1 mm.

3. The device according to claim 1, wherein the solid coating further contains a buffering substance.

4. The device according to claim 1, wherein the solid coating further conatins an anti-coagulant substance.

5. The device according to claim 1, wherein the solid coating further contains a stabilizing substance.

* * * * *